United States Patent
Strauss et al.

(10) Patent No.: US 9,393,038 B2
(45) Date of Patent: Jul. 19, 2016

(54) HIGH FREQUENCY SURGICAL DEVICE AND HIGH FREQUENCY SURGICAL SYSTEM WITH A VOLTAGE LIMITER

(75) Inventors: Timo Strauss, Gernlinden (DE); Uwe Fischer, Berlin (DE); Stefan Schiddel, Potsdam (DE); Antonios Patelis, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 24 days.

(21) Appl. No.: 13/985,456

(22) PCT Filed: Feb. 15, 2012

(86) PCT No.: PCT/EP2012/052559
§ 371 (c)(1),
(2), (4) Date: Aug. 14, 2013

(87) PCT Pub. No.: WO2012/116891
PCT Pub. Date: Sep. 7, 2012

(65) Prior Publication Data
US 2013/0325002 A1 Dec. 5, 2013

Related U.S. Application Data

(60) Provisional application No. 61/450,905, filed on Mar. 9, 2011.

(30) Foreign Application Priority Data

Mar. 3, 2011 (DE) .......................... 10 2011 005 067

(51) Int. Cl.
*A61B 18/12* (2006.01)
*A61B 17/3203* (2006.01)
(Continued)

(52) U.S. Cl.
CPC ............. *A61B 17/3203* (2013.01); *A61B 18/00* (2013.01); *A61B 18/1206* (2013.01);
(Continued)

(58) Field of Classification Search
CPC .... A61B 18/10; A61B 18/12; A61B 18/1206; A61B 18/1233; A61B 18/14; A61B 18/1402; A61B 2018/00702; A61B 2018/00892; A61B 2018/00601; A61B 2018/00607; A61B 2018/00589; A61B 2018/00595; A61B 2018/0001; A61B 2018/00779; A61B 2018/1213
USPC ................................. 606/33–45; 607/98–102
See application file for complete search history.

(56) References Cited

U.S. PATENT DOCUMENTS 4,901,183 A * 2/1990 Lee ........................ H02H 9/042
361/111
5,522,814 A 6/1996 Bernaz
(Continued)

FOREIGN PATENT DOCUMENTS

| CN | 1768714 A | 5/2006 |
| CN | 101106950 A | 1/2008 |

(Continued)

OTHER PUBLICATIONS

May 16, 2012 Search Report issued in International Patent Application No. PCT/EP2012/052559.

(Continued)

*Primary Examiner* — Ronald Hupczey, Jr.
*Assistant Examiner* — Khadijeh Vahdat
(74) *Attorney, Agent, or Firm* — Oliff PLC

(57) ABSTRACT

A high frequency surgical device for generating a high frequency voltage for cutting and/or vaporizing biological tissue within a flushing liquid, in particular a conductive flushing liquid, including two output contacts at which an electrosurgical instrument is connectable and between which the HF voltage is provided during operations; a parallel resonant circuit which is electrically connected with the output contacts and in which the HF voltage is generated during operations, and wherein the HF voltage is configured for igniting an electric arc within the flushing liquid at the electrosurgical instrument. In order to provide an electrosurgical device for applications under a flushing liquid, wherein the flushing liquid is heated less and wherein the electrosurgical device provides better initial cutting properties, it is provided according to the invention that a voltage limiter is arranged between the parallel resonant circuit and the output contacts.

10 Claims, 5 Drawing Sheets

(51) Int. Cl.
*A61B 18/00* (2006.01)
*A61B 18/14* (2006.01)

(52) U.S. Cl.
CPC ........... *A61B2018/00625* (2013.01); *A61B 2018/00678* (2013.01); *A61B 2018/00767* (2013.01); *A61B 2018/00892* (2013.01); *A61B 2018/1213* (2013.01); *A61B 2018/1253* (2013.01); *A61B 2018/1472* (2013.01)

(56) References Cited

U.S. PATENT DOCUMENTS

| | | | |
|---|---|---|---|
| 5,633,578 A | | 5/1997 | Eggers et al. |
| 5,658,277 A | * | 8/1997 | Marshall et al. ............ 606/34 |
| 5,713,925 A | * | 2/1998 | Sullivan et al. ............ 607/4 |
| 6,261,286 B1 | | 7/2001 | Goble et al. |
| 2008/0147057 A1 | | 6/2008 | Eisele |
| 2012/0165816 A1 | * | 6/2012 | Kersten et al. ............ 606/45 |

FOREIGN PATENT DOCUMENTS

| | | |
|---|---|---|
| DE | 10 2008 055 820 B3 | 4/2010 |
| JP | H04-500298 A | 1/1992 |
| JP | H09-10223 A | 1/1997 |
| WO | 90/02431 A1 | 3/1990 |
| WO | WO 01/06941 A1 | 2/2001 |

OTHER PUBLICATIONS

May 16, 2012 Written Opinion issued in International Patent Application No. PCT/EP2012/052559.
Mar. 25, 2015 Office Action issued in Chinese Patent Application No. 201280011400.1.
Jul. 21, 2015 Office Action issued in Japanese Patent Application No. 2013-555816.
Nov. 18, 2015 Office Action issued in Chinese Patent Application No. 201280011400.1.
Translation of Mar. 28, 2016 Office Action issued in Japanese Patent Application No. 2013-555816.

* cited by examiner

HIGH FREQUENCY SURGICAL DEVICE AND HIGH FREQUENCY SURGICAL SYSTEM WITH A VOLTAGE LIMITER

The invention relates to a HF surgical device for generating a HF-voltage for cutting and/or vaporizing biological tissue within a flushing liquid, in particular a conductive flushing liquid. The HF surgical device includes two output contacts at which an electro surgical instrument is connectable and between which the HF voltage is provided during operations and a parallel resonant circuit which is electrically connected with the output contacts and in which the HF voltage is generated during operations. The provided HF voltage is configured to ignite an arc at the electrosurgical instrument, wherein the electrosurgical instrument is disposed in the flushing liquid.

Furthermore the invention also relates to a HF-surgical system for cutting and/or vaporizing biological tissue within a flushing liquid in particular a conductive flushing liquid. The system includes a HF surgical device for generating a HF voltage, wherein the HF surgical device includes two output contacts and a parallel resonant circuit that is electrically connected with the output contacts and an electro surgical instrument. The instrument includes an active electrode which is electrically connected with one of the output contacts and wherein HF voltage is provided at the active electrode during operations for igniting an electric arc within the flushing liquid.

HF surgical devices and HF surgical systems of this type are known in the art. They are being used for example in urology or gynecology. Thus, e.g. for TURiS (Transuretale Resection in Saline)-Plasma-Vaporization for treating benign prostate enlargements.

Thus, an electric arc is ignited at the cutting electrode of a suitable instrument like a resktoskope, thus the cutting electrode is arranged in a conductive flushing liquid like e.g. a saline solution (NaCl).

Igniting an electric arc or a plasma places particular requirements upon the HF surgical device, also designated HF surgical generator or HF generator for HF surgical applications under a flushing liquid, in particular a conductive flushing liquid. In order to ignite the electric arc a vapor layer has to be generated about the cutting electrode. In order to generate the vapor layer high powers and currents are required. On the other hand side excessive power output shall be prevented because this can strongly heat the flushing liquid. A strongly heated flushing liquid on the other hand side yields the risk of unintentional thermal tissue damage.

Prior art HF surgical devices therefore put out very high power to the cutting electrode only for a short period of time in order to facilitate immediate igniting of the electric arc. Subsequently they put out little to no power in order to prevent excessive heating of the flushing liquid. After igniting the electric arc the power is reduced to an acceptable level due to the voltage-/resistance ratio during electric arc discharge. Therefore quick igniting of the electric arc is desirable.

Thus it is an object of the present invention to provide a HF surgical device and system for an application under a flushing liquid in which the flushing liquid is heated up as little as possible and which provides improved initial cutting properties.

This technical problem is solved through the object of the independent claims.

The solution includes identifying the technical problem that large amounts of energy are stored in the resonant output circuit for the recited HF surgical devices and HF surgical systems with a parallel resonant circuit during the ignition phase which is characterized by high current and low voltage. In this case the output circuit is the parallel resonant circuit. As soon as a vapor layer has formed at the active electrode of the instrument the resistance increases quickly. Through the increased resistance the voltage is increased which facilitates the electric arc discharge. However, voltage peaks briefly occur through the energy stored in the output circuit, wherein the voltage peaks are greater than required for a stable electric arc discharge.

Through the voltage peaks more energy than necessary is released during electric arc discharge which makes the vapor layer about the active electrode excessively large so that it almost completely separates from the electrode in a form of gas bubbles. The separation of the vapor layer from the electrode in turn has the consequence that the electric arc and the electric arc discharge collapse. After the collapse of the electric arc a new ignition cycle is required in order to reignite the electric arc. Continuous collapsing and reigniting of the electric arc degrades the initial cutting properties of the instrument. The quality of the initial cutting properties is mainly determined by the time span from the contact of the electrode with the tissue to be cut until a stable electric arc discharge is formed which achieves the desired tissue separating effect, thus which is used for cutting.

Inferior initial cutting properties with a long time span until cutting is performed overall can lead to extended surgery times. Furthermore reigniting the electric arc can lead to an increased heating of the flushing liquid.

FIG. 1 illustrates this problem based on the voltage diagram over time. Initially, the HF output voltage $U1$ is small. Through the increased resistance through the formed steam layer as recited supra the voltage increases by a large amount to the excessively high value $U3$ through the energy stored in the output circuit. Through the resulting excessive energy input, the vapor layer separates from the electrode, so that the electric arc collapses and the voltage drops to the initial level $U1$. The process repeats itself until a stable electric arc discharge with a suitable HF voltage $U2$ is reached.

The HF surgical device according to the invention solves the problem in that a voltage limiter is arranged between the parallel resonant circuit and the output contacts.

The HF surgical device according to the invention solves the problem in that the system includes a voltage limiter which is arranged between the parallel resonant circuit and the active electrode.

The solution according to the invention has the advantage that the voltage limiter limits the HF voltage which is applied to the instrument or the electrode to a predetermined level that is configured for igniting the electric arc or transposes the HF voltage in another manner. This level is high enough to provide ignition for the electric arc and low enough to keep the vapor layer about the electrode small so that good initial cutting properties are provided.

Since the voltage limiter is arranged subsequent to the parallel resonant circuit, the energy stored in the parallel resonant circuit is limited as well. Without the present invention, the stored energy could lead to high voltage peaks.

This is an advantage over alternative solutions in the art, like e.g. DE 10 2008 055820, which omit a parallel resonant circuit. The solution presented herein also includes the finding that voltage peaks of this type cannot be prevented through a prior art regulation of the output voltage of the HF surgical device since the amount of energy stored in the parallel resonant circuit cannot be subsequently influenced through a control variable.

The invention can be improved through advantageous embodiments which are subsequently described. The features of the embodiment are randomly combinable with one another.

Thus, the HF surgical device can include a regulator for regulating the HF voltage at the output contacts, wherein the regulator uses the HF voltage limited by the voltage limiter as a regulation parameter. This has the advantage that the regulator operates with the HF voltage that is smoothed not to have voltage peaks, thus the HF voltage is measured behind the voltage limiter. In the prior art HF generators recited supra it is not possible to avoid voltage peaks through regulating the output voltage. The amount of energy once stored in the parallel resonant circuit cannot be influenced subsequently through the available regulation variables. To the contrary, the regulator makes the problem worse because the voltage collapses through the separating vapor layer and the regulator additionally regulates the voltage down. Thus it takes particularly long until another electric arc ignites.

In another advantageous embodiment, the voltage limiter can limit the HF voltage to a maximum of 400 to 460 Vp (Vp: volt peak), in particular 450 Vp. Experiments have proven that this HF voltage is sufficiently high for igniting the electric arc and on the other hand side sufficiently low so that the vapor layer does not separate from the electrode.

In order to quickly prevent that the flushing liquid heats up and in order to keep the heat volume that is put out low, the voltage limiter can limit the voltage within a time span of less than 10 ms.

In order for the HF surgical device to also to be usable for applications in which voltage peaks or higher voltages are desirable, the HF surgical device can include a switch through which the voltage limiter can be optionally switched on.

In an advantageous embodiment of the invention the voltage limiter can be a TVS-diode or a Varistor. This has the advantage that the components are easily and economically available.

The invention also relates to a method for cutting and/or vaporizing biological tissue within a cooling liquid, in particular a conductive cooling liquid. The method includes the following steps: generating a HF voltage in a parallel resonant circuit of a HF surgical device; removing voltage peaks which are above a predetermined peak voltage and which last longer than 10 ms at the most from the HF voltage; applying the HF voltage between an active electrode of an electrosurgical instrument and the tissue within the flushing liquid; cutting and/or vaporizing the tissue through an electric arc to be ignited between the active electrode and the tissue.

The invention is subsequently described with reference to preferred embodiments illustrated in drawing figures. The features are combinable in a random manner.

Initially, the invention is described with reference to the embodiment in FIG. 2.

Figure 1:
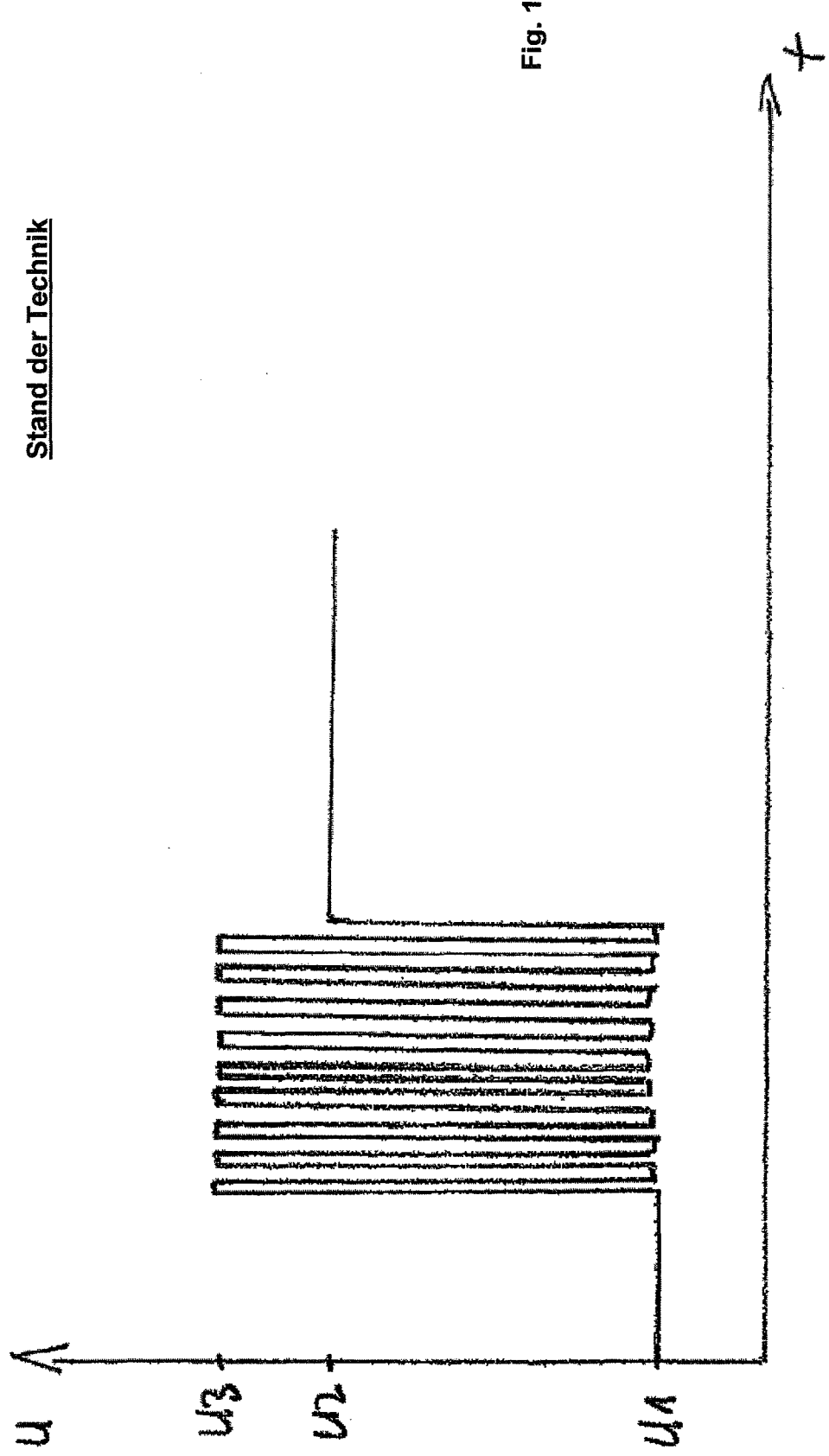
FIG. 1 illustrates a diagram of the HF output voltage of a prior art HF surgical device.
Figure 2:
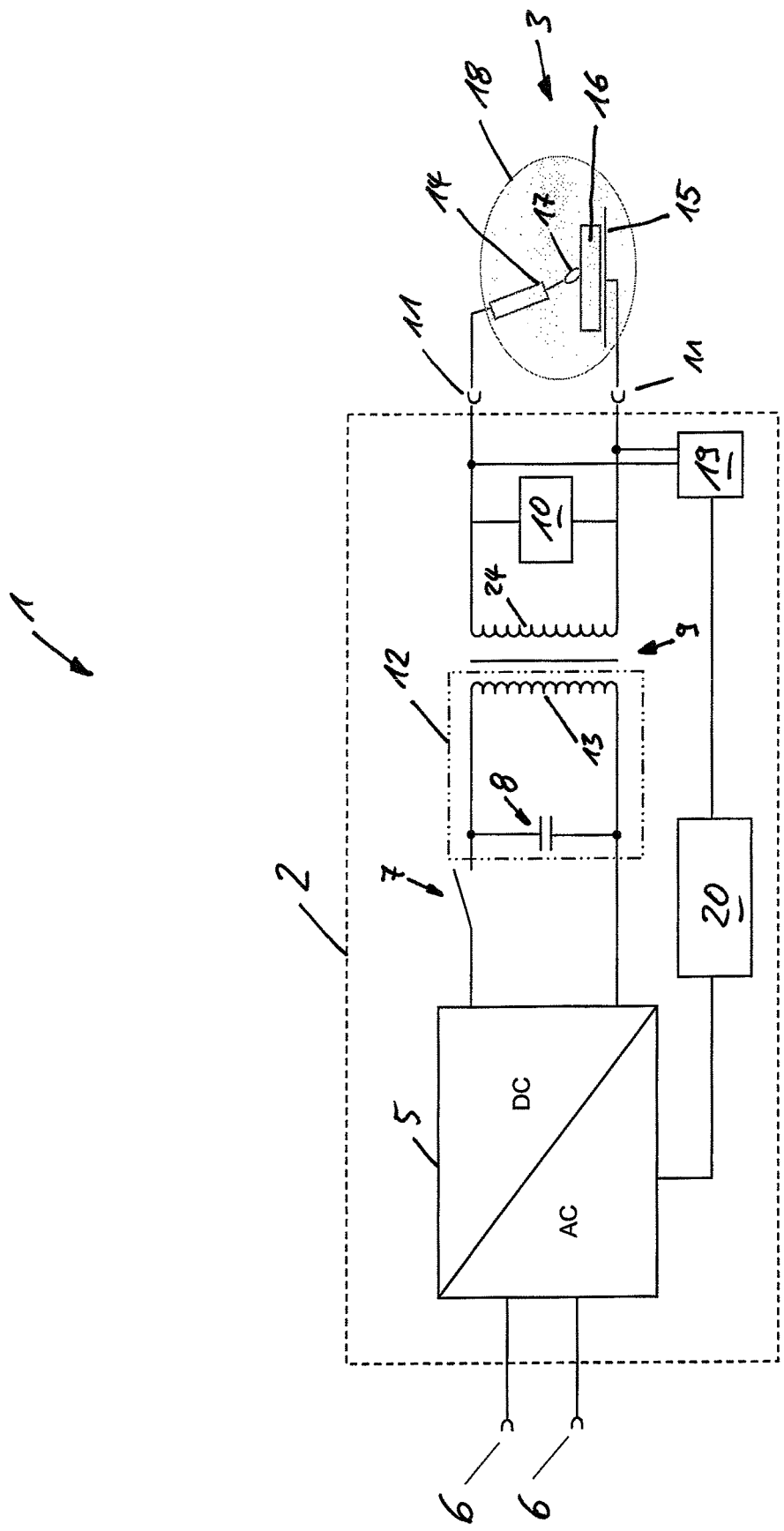
FIG. 2 illustrates a schematic view of an embodiment of a HF surgical device according to the invention and a HF surgical system according to the invention.

FIG. 2 illustrates a HF surgical system 1 which includes a HF surgical device 2 and an electrosurgical instrument 3.

The HF surgical device 2 which is only schematically illustrated includes a power supply 5, electric grid contacts 6, a switch 7, a capacitance 8, a transformer 9, a voltage limiter 10, a voltage measuring device 19, a regulator 20 and output contacts 11.

The power supply 5 is connectable on the input side through grid contacts 6 with a power grid (not illustrated). On the output side, the power supply 5 is connected with a parallel resonant circuit 12. The parallel resonant circuit 12 is formed by the capacitance 8 and the inductivity of the primary side 13 of the transformer 9 arranged parallel thereto. A switch 7 is arranged in the circuit between the parallel resonant circuit 12 and the power supply 5. The secondary side 24 of the transformer 9 is connected with the output contacts 11.

Between the transformer 9 and the output contacts 11, a voltage limiter 10 is arranged in parallel. Thus, the voltage limiter 10 is arranged in the HF surgical device 2 according to the invention between the parallel resonant circuit 12 and the output contacts 11. In the HF surgical system 1 according to the invention, the voltage limiter 10 is arranged between the parallel resonant circuit 12 and the active electrode 14.

The voltage measuring device 19 is also arranged in parallel between the transformer 9 and the output contacts 11, however behind the voltage limiter 10. The regulator 20 is signal connected with the voltage measuring device 19 and also with the power supply 5. The electrosurgical instrument 2 that is connected with the output contacts 11 of the HF surgical device 2 includes an active electrode 14 and a return conduction electrode 15.

During operations, the HF surgical device generates a HF voltage at the output contacts 11, wherein the HF voltage is conducted to the connected instrument 3. The electrosurgical instrument 3 and the biologic tissue 16 to be treated are thus disposed within a conductive liquid 18 like e.g. a saline solution. The HF voltage is generated by the HF surgical device 2 so that an electric arc 17 is ignited between the active electrode 14 and the biologic tissue 16 to be treated. Through the return conduction electrode 15, the current flows back to the HF surgical device 2.

In order to generate a suitable HF voltage, initially the grid voltage applied to the grid contacts 16 is converted into a DC voltage in the power supply 5 in the HF surgical device 2. The DC voltage applied to the output of the power supply 5 is fed into the parallel resonant circuit 12 in a pulsed manner. Thus, the switch 7 opens and closes in order to generate the DC voltage pulses. The switch 7 is controlled by a control unit (not illustrated) of the HF surgical device 2 with a fixed or variable frequency. This generates the HF voltage with the desired frequency in the parallel resonant circuit 12, thus between 300 kHz and 2 MHz. Certainly also plural switches 7 can be provided which feed the DC voltage with different switching frequencies into the parallel resonant circuit 12 in order to generate e.g. a modulated HF voltage.

The HF voltage generated in the parallel resonant circuit 12 is extracted through the transformer 9 during operations and conducted to the output contacts 11 in order to generate the electric arc 17 at the instrument 3.

Figure 3:
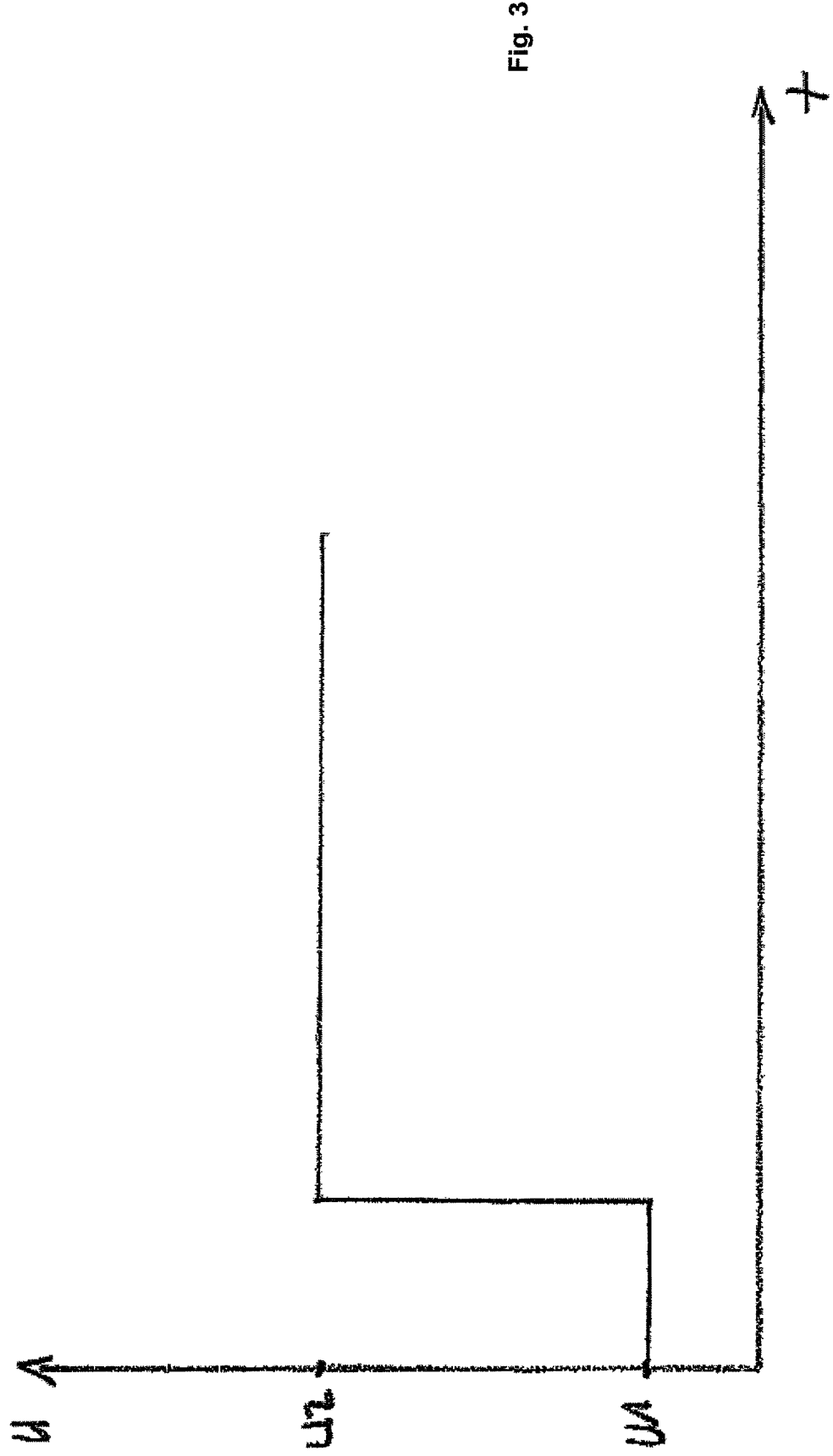
FIG. 3 illustrates a diagram of the HF output voltage of the HF surgical device of FIGS. 2 and 4.

During the ignition phase of the electric arc 17, a large amount of energy is stored in the parallel resonator 12. As soon as a vapor layer (not illustrated) has formed at the active electrode 14 of the instrument 3, the resistance increases over a short time period. The HF voltage increases through the increased resistance which ignites the electric arc 17. In order to prevent voltage peaks U3 as illustrated in FIG. 3 which could influence the stability of the electric arc 17 negatively and which can occur over short time periods through the energy stored in the parallel resonant circuit 12, the voltage limiter 10 is provided in the HF surgical device 2 according to the invention. The voltage limiter 10 limits the HF voltage upward and converts the voltage above a predetermined level U2 in another manner like e.g. into heat energy. Thus, the peak of the HF voltage is reliably limited to a value U2 that is configured for a stable electric arc 17 as illustrated in FIG. 3.

Thus, the voltage limiter 10 is configured in the exemplary embodiment in FIG. 2 so that it limits HF voltages above 450 Vp within a time period that is shorter than 10 ms.

In order to regulate the HF voltage at the output contacts 11, the HF surgical device 2 includes the regulator 20 in combination with the voltage measuring device 19. The voltage measuring device 19 measures the HF voltage limited by the voltage limiter and conducts a representative signal to the regulator 20. The regulator 20 compares the signal from the voltage measuring device 19 with a predetermined target value and controls the power supply 5.

The method according to the invention for cutting and/or vaporizing biological tissue 16 within a liquid, in particular the conducting liquid 18 includes the following steps: initially a HF voltage is generated in the parallel resonant circuit 12 of the HF surgical device 2. Subsequently voltage peaks which are above a predetermined peak voltage and which last longer than 10 ms at the most are removed. Subsequently the HF voltage from which the voltage peaks are removed is provided at the output contacts 11 of the HF surgical device 2. From the output contacts 11, the HF voltage is provided to an electrosurgical instrument 3. Eventually, the tissue 16 is cut and/or vaporized by an electric arc 17 that is burning between the instrument 3 and the tissue 16.

Figure 4:
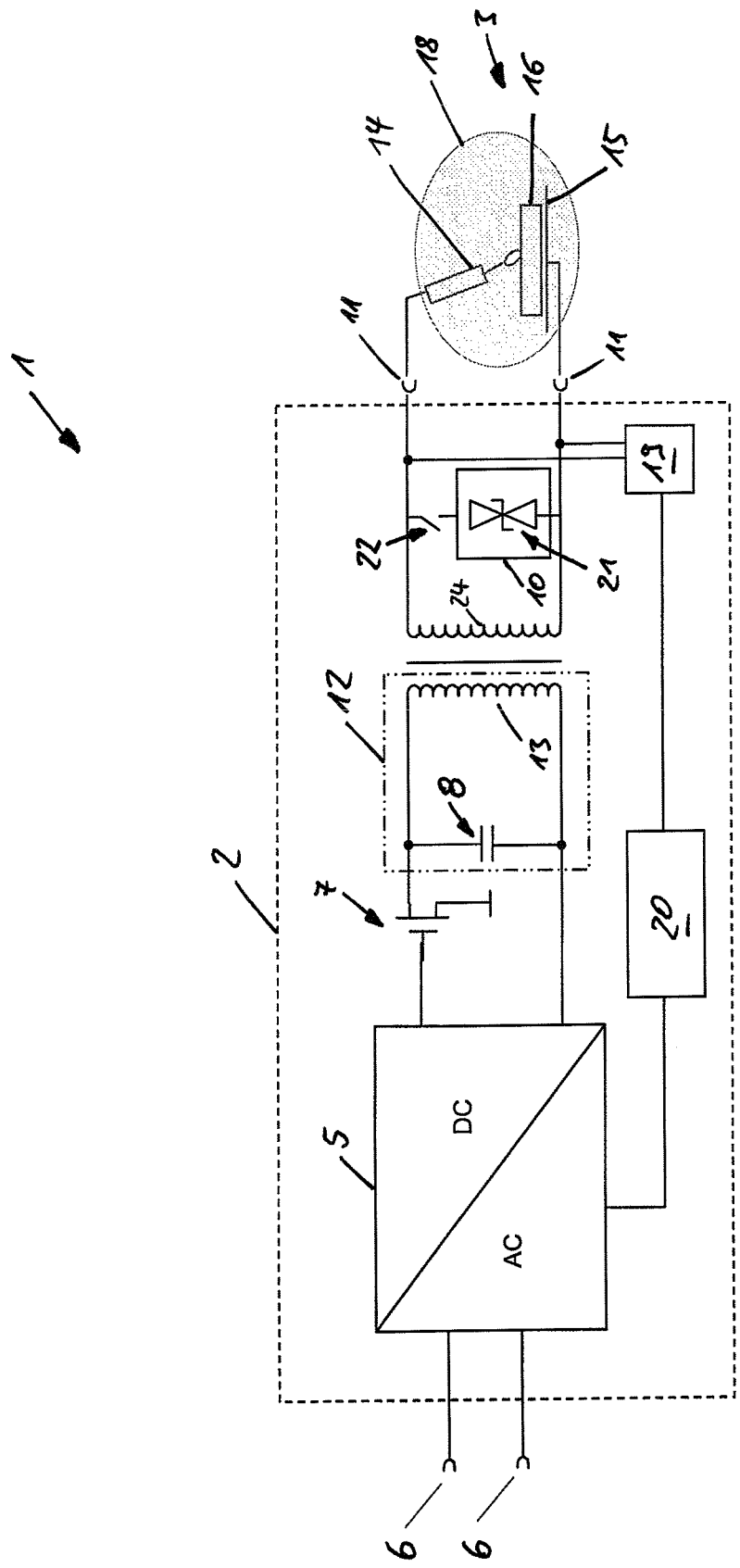
FIG. 4 illustrates a schematic view of another embodiment of an HF surgical device according to the invention and of an HF surgical system.

Subsequently, an additional embodiment of the system 1 according to the invention is described as illustrated in FIG. 4. For reasons of simplicity, only the differences to the embodiment in FIG. 2 are described. Like components are provided with like reference numerals.

In the embodiment in FIG. 4, the switch 7 is configured as a transistor which can be switched very quickly by the control unit. Furthermore, the voltage limiter 10 includes a TVS diode 21. The TVS diode 21 has the advantage that it is available as a standard component in a very simple and cost-effective manner and that it limits the voltage very quickly, this means quicker than 10 ms. Alternatively, the voltage limiter 10 can also include e.g. a Varistor. Furthermore, the HF surgical device 2 in FIG. 4 includes a switch 22 through which the voltage limiter 10 is variably switchable.

Figure 5:
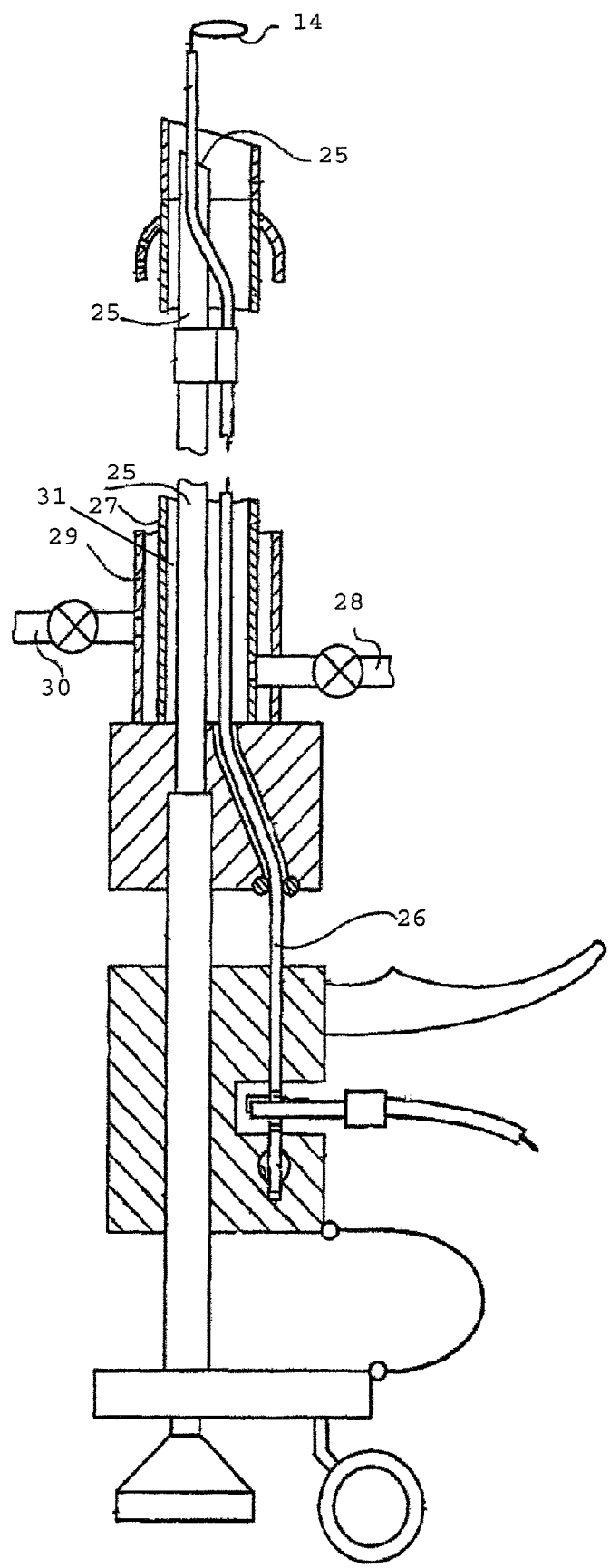
FIG. 5 illustrates an electrosurgical instrument configured as a resectoscope.

FIG. 5 illustrates an exemplary resectoscope configured as an electrosurgical instrument 3 in a detailed view. In a resectoscope, the optics 25 facilitate tissue extraction during optical viewing by a surgeon. In order to separate (cut) tissue to be extracted, the active electrode 14 of the electrosurgical instrument 3 is used. The active electrode 14 is arranged at a distal end of an electrical conductor 26 and can be connected through the electrical conductor with the output contact 11 of the electrosurgical device.

The optics 25 are enveloped by a shaft tube 27, whose interior is used as a feed channel 31 for flushing liquid and which includes a connection 28 for connecting a flushing liquid source through a respective hose for this purpose. The shaft tube 27 is enveloped by an exterior tube 29. Between the shaft tube 27 and the interior tube 29, there is a cavity with an annular cross-section which is therefore also designated as a ring channel and is used as a return channel for extracting flushing liquid. The ring channel also includes a connection 30 which can be connected through a hose with an extraction pump. The extraction pump can be a component of the flushing liquid source.

The invention claimed is:

1. A high frequency surgical device for generating a high frequency voltage for cutting or vaporizing of biological tissue during operations within a flushing liquid, the high frequency surgical device comprising:
two output contacts at which an electrosurgical instrument is connectable and between which the high frequency voltage is provided during the operations;
a parallel resonant circuit which is electrically connected with the two output contacts and in which the high frequency voltage is generated during the operations, wherein the high frequency voltage is configured for igniting an electric arc within the flushing liquid at the electrosurgical instrument, wherein a voltage limiter is arranged between the parallel resonant circuit and the two output contacts, wherein the voltage limiter is arranged parallel to the two output contacts, and wherein a voltage measuring device is arranged in parallel to the voltage limiter and the two output contacts, said voltage measuring device being distinct from said voltage limiter.

2. The high frequency surgical device according to claim 1, wherein the high frequency surgical device includes a regulator for regulating the high frequency voltage at the two output contacts, wherein the regulator uses the high frequency voltage limited by the voltage limiter as a control variable.

3. The high frequency surgical device according to claim 1, wherein the voltage limiter is configured to limit the high frequency voltage to a maximum of 400 to 460 Vp.

4. The high frequency surgical device according to claim 1, wherein the voltage limiter is configured to limit the high frequency voltage within a time period of less than 10 ms.

5. The high frequency surgical device according to claim 1, wherein the high frequency surgical device includes a switch through which the voltage limiter is optionally switchable.

6. The high frequency surgical device according to claim 1, wherein the voltage limiter is a TVS diode.

7. The high frequency surgical device according to claim 1, wherein the voltage limiter is a varistor.

8. A high frequency surgical system for cutting or vaporizing of biological tissue during operations within a flushing liquid, the high frequency surgical system comprising
a high frequency surgical device for generating a high frequency voltage including two output contacts and a parallel resonator electrically connected with the two output contacts; and
an electrosurgical instrument, wherein the electrosurgical instrument includes an active electrode which is electrically connected with one of the two output contacts and at which the high frequency voltage for igniting an electric arc is provided within the flushing liquid during the operations, wherein the high frequency surgical system includes a voltage limiter which is arranged between the parallel resonant circuit and the active electrode, wherein the voltage limiter is arranged parallel to the two output contacts, and wherein a voltage measuring device is arranged in parallel to the voltage limiter and the two output contacts, said voltage measuring device being distinct from said voltage limiter.

9. The high frequency surgical system according to claim 8, wherein the voltage limiter is a TVS diode or a varistor.

10. The high frequency surgical system according to claim 8, wherein the electrosurgical instrument includes at least one flushing liquid channel for moving the flushing liquid proximal to the active electrode, wherein the at least one flushing liquid channel is connected with a flushing liquid source during operation of the high frequency surgical system.

\* \* \* \* \*